US008585600B2

(12) United States Patent
Liu et al.

(10) Patent No.: US 8,585,600 B2
(45) Date of Patent: Nov. 19, 2013

(54) ULTRASOUND VOLUME PROBE NAVIGATION AND CONTROL METHOD AND DEVICE

(75) Inventors: Gang Liu, Wuxi (CN); Houbing Liu, Beijing (CN); Yiming Zhao, Beijing (CN); Weidong Zhao, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 54 days.

(21) Appl. No.: 13/315,055

(22) Filed: Dec. 8, 2011

(65) Prior Publication Data
US 2012/0150039 A1    Jun. 14, 2012

(30) Foreign Application Priority Data
Dec. 9, 2010   (CN) .......................... 2010 1 0586798

(51) Int. Cl.
*A61B 8/00* (2006.01)

(52) U.S. Cl.
USPC ........................................... 600/443; 600/437

(58) Field of Classification Search
USPC .................................. 600/437, 441, 443, 453
See application file for complete search history.

(56) References Cited

U.S. PATENT DOCUMENTS

| 6,048,317 | A | 4/2000 | Langguth |
| 6,390,984 | B1 | 5/2002 | Pan et al. |
| 6,423,006 | B1 | 7/2002 | Banjanin |
| 7,636,088 | B2* | 12/2009 | Nomura et al. ............... 345/419 |
| 2005/0124885 | A1* | 6/2005 | Abend et al. .................. 600/443 |

* cited by examiner

*Primary Examiner* — Michael Rozanski
(74) *Attorney, Agent, or Firm* — Armstrong Teasdale LLP

(57) ABSTRACT

An ultrasound volume probe navigation and control method is provided. The method includes acquiring scan data in a three-dimensional scan mode, forming a navigation view based on a three-dimensional matrix formed by the scan data in beam space, determining a critical area on the navigation view, and navigating and controlling the ultrasound volume probe based on whether a blood vessel is in the critical area.

20 Claims, 4 Drawing Sheets

ULTRASOUND VOLUME PROBE NAVIGATION AND CONTROL METHOD AND DEVICE

CROSS REFERENCE TO RELATED APPLICATIONS

This application claims the benefit of Chinese Patent Application No. 201010586798.4 filed Dec. 9, 2010, which is hereby incorporated by reference in its entirety.

BACKGROUND OF THE INVENTION

The present invention relates in general to the field of ultrasound, and in particular to an ultrasound volume probe navigation and control method and device as well as ultrasound apparatus.

Ultrasound apparatus plays a vitally important auxiliary role in the field of medical diagnosis. A clear scan of the blood vessel and blood flow can be performed through ultrasound. Conventional scan modes are all based on two-dimensional ultrasound mode, i.e. scanning only one side, thus being unable to present a three-dimensional image of the subject being scanned. For example, U.S. Pat. Nos. 6,423,006, 6,048,317, and 6,390,984 are all based on two-dimensional ultrasound mode.

The three-dimensional scan mode has an advantage over the two-dimensional scan mode. In a two-dimensional scan mode, the user has to move the probe time after time to acquire a proper sectional view of the blood vessel, but the three-dimensional scan mode can present the whole subject being scanned, e.g., the overall image of the blood vessel, thus making it more convenient for the doctor to diagnose the subject being scanned and carry out subsequent treatment. However, the three-dimensional scan mode also requires the user to put the volume probe in the correct area, and if the user cannot keep the volume probe always in a proper area, the vessel tracking may fail, and no overall vessel image can be obtained. This is because the blood vessel has gone beyond the scan range of the volume probe.

How to navigate and control the scanned subject, such as blood vessel, in a three-dimensional scan mode is one of the key points of industry research at present.

SUMMARY OF THE INVENTION

An ultrasound volume probe navigation and control method and device as well as an ultrasound apparatus are provided that are capable of correctly tracking the blood vessel.

In one aspect, an ultrasound volume probe navigation and control method is provided. The ultrasound volume probe navigation and control method includes acquiring scan data in a three-dimensional scan mode, forming a navigation view based on a three-dimensional matrix formed by the scan data in beam space, determining a critical area on the navigation view, and navigating and controlling the ultrasound volume probe according to whether the blood vessel is in the critical area.

Furthermore, the method includes displaying said navigation view on a display in real time.

The scan data can be expressed as:

$$N_{samples} \times N_{beams} \times N_{frames}$$

wherein, $N_{samples}$ indicates the number of samples on each beam, $N_{beams}$ indicates the number of beams, and $N_{frames}$ indicates the number of frames being scanned when the ultrasound volume probe sweeps.

In one embodiment, the ultrasound volume probe navigation and control method further includes creating a mathematical model of the blood vessel in the scan direction based on the three-dimensional matrix.

The mathematical model can be expressed as:

$$\frac{(x\cos\theta + y\sin\theta)^2}{a^2} + \frac{(y\cos\theta - x\sin\theta)^2}{b^2} = 1$$

wherein a indicates the major axis of the ellipse, b indicates the minor axis of the ellipse, and θ indicates the angle between the major axis of the ellipse and the coordinate axis X.

In one embodiment, the ultrasound volume probe navigation and control method further includes calculating, through the following formula, the projection on the X coordinate axis of a point on the boundary curve of the blood vessel:

$$P_X = |a \cos\theta \cos\alpha - b \sin\theta \sin\alpha|$$

wherein, $$\tan\alpha = \frac{b}{a}\tan\theta.$$

In one embodiment, when the boundary curve of the blood vessel has an intersection with the critical area, a warning is sent.

The warning includes changing the color of the critical area.

The warning includes making the speaker produce sound.

In addition, if blood vessel enters the critical area, the scan range is changed so that the blood vessel can be included in the scan volume range.

In another aspect, an ultrasound volume probe navigation and control device is provided. The ultrasound volume probe navigation and control device includes a unit for acquiring scan data in a three-dimensional scan mode, a unit for forming a navigation view based on a three-dimensional matrix formed by the scan data in beam space, a unit for determining a critical area on the navigation view, and a unit for navigating and controlling the ultrasound volume probe according to whether the blood vessel is in the critical area.

The device further includes a unit for displaying the navigation view on a display in real time.

The scan data can be expressed as:

$$N_{samples} \times N_{beams} \times N_{frames}$$

wherein Nsamples indicates the number of samples on each beam, Nbeams indicates the number of beams, and Nframes indicates the number of frames being scanned when the ultrasound volume probe sweeps.

In one embodiment, the ultrasound volume probe navigation and control device further includes a unit for creating a mathematical model of the blood vessel in the scan direction based on the three-dimensional matrix.

The mathematical model can be expressed as:

$$\frac{(x\cos\theta + y\sin\theta)^2}{a^2} + \frac{(y\cos\theta - x\sin\theta)^2}{b^2} = 1$$

wherein a indicates the major axis of the ellipse, b indicates the minor axis of the ellipse, and θ indicates the angle between the major axis of the ellipse and the coordinate axis X.

In one embodiment, the ultrasound volume probe navigation and control device further includes a unit for calculating, through the following formula, the projection on the X coordinate axis of a point on the boundary curve of the blood vessel:

$$P_X = |a \cos\theta \cos\alpha - b \sin\theta \sin\alpha|$$

wherein, $$\tan\alpha = \frac{b}{a}\tan\theta.$$

In one embodiment, the ultrasound volume probe navigation and control device further includes a unit for sending a warning when the boundary curve of the blood vessel has an intersection with the critical area.

The warning includes changing the color of the critical area or making the speaker produce sound.

In one embodiment, the ultrasound volume probe navigation and control device further includes a unit for changing the scan range, if the blood vessel enters the critical area, so that the blood vessel can be included in the scan volume range.

In another aspect, an ultrasound apparatus is provided. The ultrasound apparatus includes an ultrasound volume probe navigation and control device.

Compared with the prior art, the embodiments described herein have a number of beneficial effects.

Firstly, the embodiments described herein adopt a three-dimensional scan mode and form a navigation view based on a three-dimensional matrix formed by the obtained scan data in beam space, thereby being able to obtain the vessel positions in real time to navigate and control the volume probe, without the scenario of the blood vessel being outside the scan range.

Secondly, the embodiments described herein are able to control and adjust the scan parameters according to the vessel positions, and make a good balance between the system performance and error tolerance.

BRIEF DESCRIPTION OF THE DRAWINGS

For a thorough understanding of the embodiments described herein, reference is made to the following drawings.

DETAILED DESCRIPTION OF THE INVENTION

Exemplary embodiments are described in detail below, but the present invention is not limited to the following embodiments.

Figure 1:
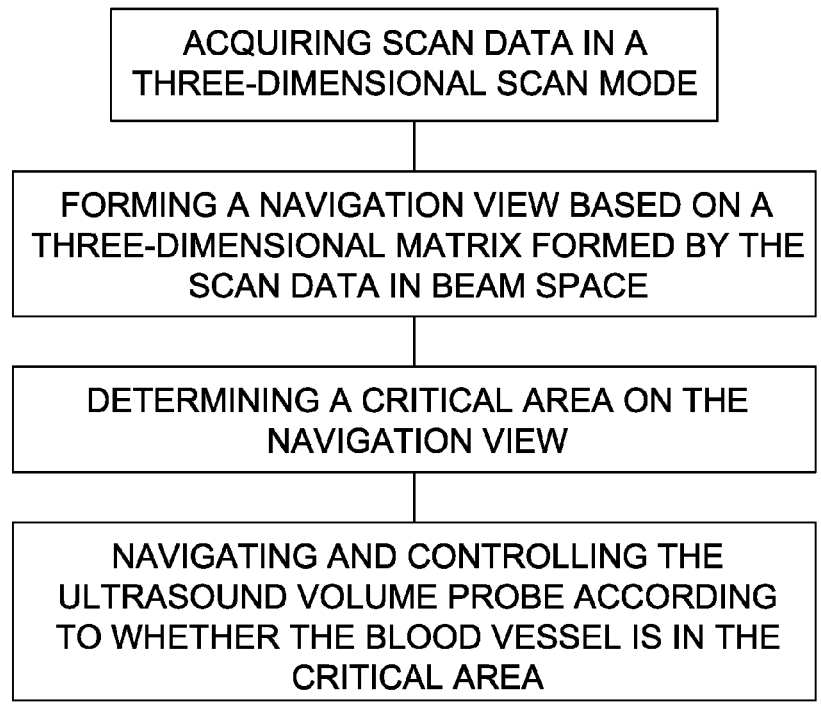
FIG. 1 is a flow chart of an exemplary ultrasound volume probe navigation and control method.

As shown in FIG. 1, an exemplary ultrasound volume probe navigation and control method includes acquiring scan data in a three-dimensional scan mode, forming a navigation view based on a three-dimensional matrix formed by the scan data in beam space, determining a critical area on the navigation view, and navigating and controlling the ultrasound volume probe according to whether the blood vessel is in the critical area.

Figure 2:
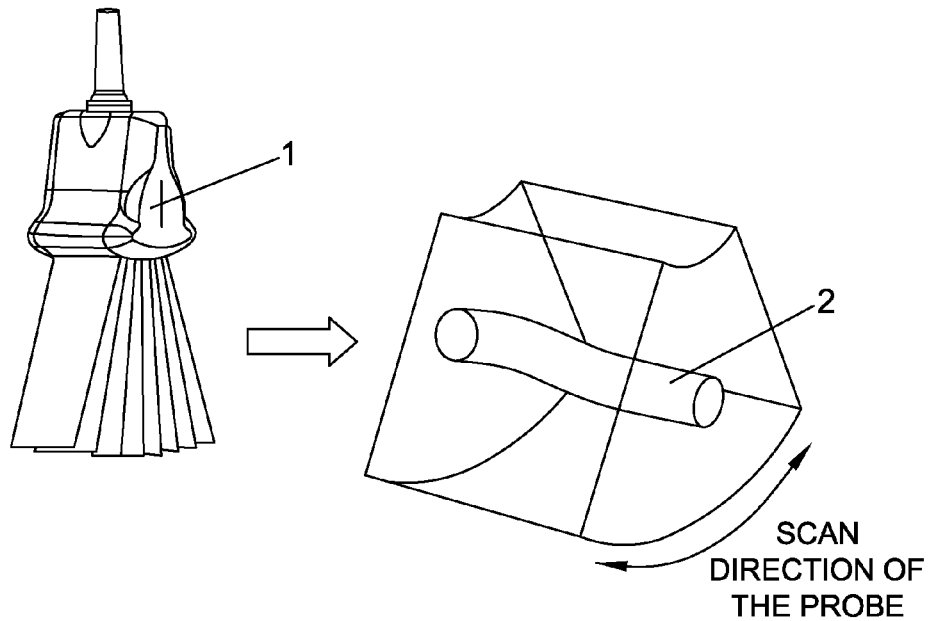
FIG. 2 is a schematic diagram illustrating scanning a blood vessel in a three-dimensional mode.
Figure 3:
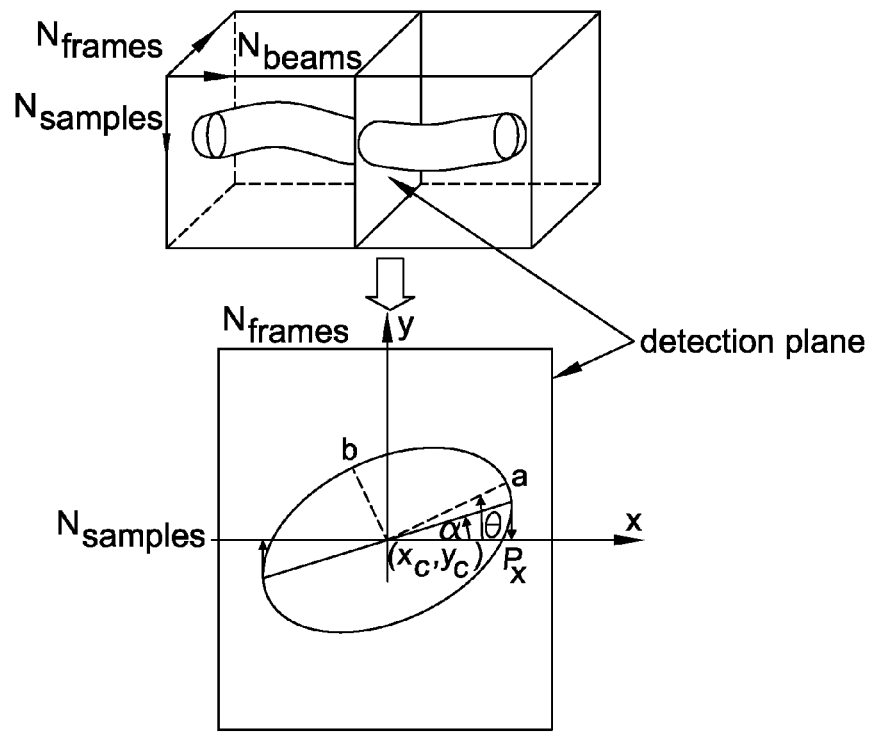
FIG. 3 is a schematic diagram of a three-dimensional matrix in beam space of the scan data obtained in a three-dimensional mode and of an elliptic mathematical model of the blood vessel within a detection plane.
Figure 4:
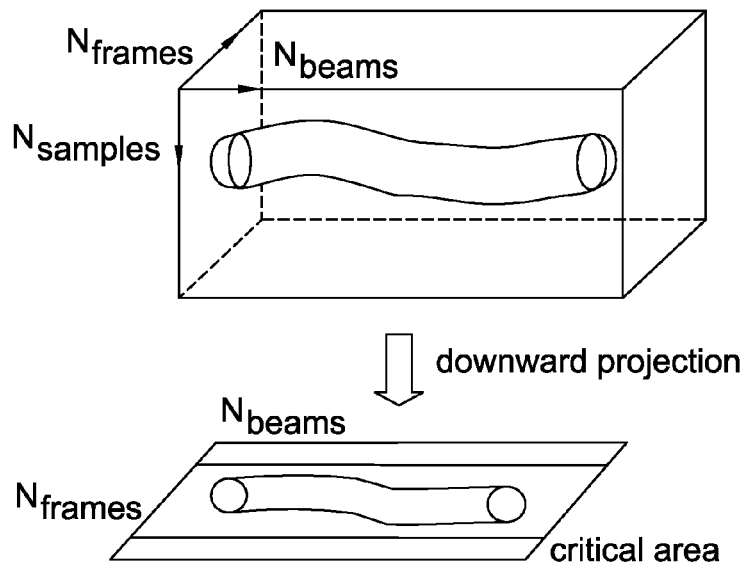
FIG. 4 is a schematic diagram illustrating obtaining a navigation view.

The ultrasound volume probe navigation and control method first acquires scan data in a three-dimensional scan mode, namely three-dimensional scan data. As shown in FIG. 2, the direction perpendicular to the blood vessel 2 lengthwise is the direction of scan, namely the ultrasound volume probe 1 sweeps within a plane formed along this direction to scan the subject. After obtaining scan data, a navigation view is formed based on a three-dimensional matrix (i.e., scan data field, as shown in FIG. 3) formed by the scan data in beam space, e.g., by making a downward projection of the three-dimensional matrix to obtain a projection view, whose width is equivalent to the number of beams of the scan data field, and height is equivalent to the number of frames of the scan data field. This projection view is a navigation view, as shown in FIG. 4, and certainly the navigation view can also be obtained by other manners known to a person having ordinary skill in the art, e.g., a three-dimensional view on the basis of a certain visual angle. With the navigation view, a critical area can be determined thereon. The critical area refers to the marginal area of the probe scan range. That is, that a blood vessel enters the critical area indicates that the blood vessel is going to move out of the scan range of the probe. The critical area can be set to be 10% of the width of the navigation view and so on, or set by the user. The critical area is a key area used to determine whether the blood vessel is in the safe scan range of the ultrasound volume probe. If the blood vessel is entering the critical area, it is indicated that the blood vessel will be outside of the scan range of the ultrasound volume probe, and corresponding measures shall be adopted to prevent the blood vessel from moving out of the scan range of the ultrasound volume probe. If the blood vessel is not in the critical area, current scan can be continued without having to be adjusted (e.g., scan parameters and so on).

Figure 5A:
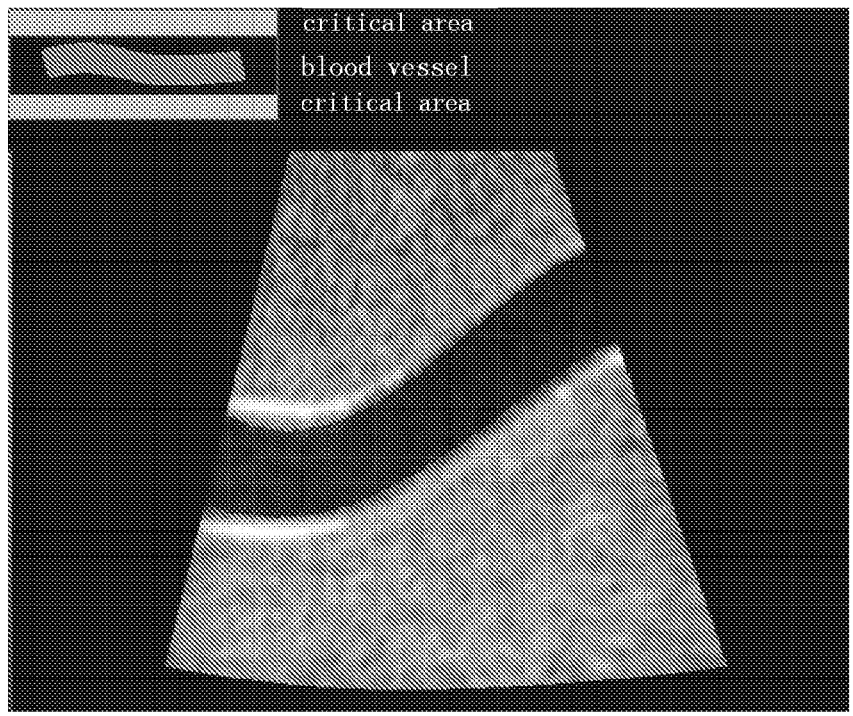
FIGS. 5A and 5B are schematic diagrams illustrating performing probe navigation according to the navigation view shown in FIG. 4.
Figure 5B:
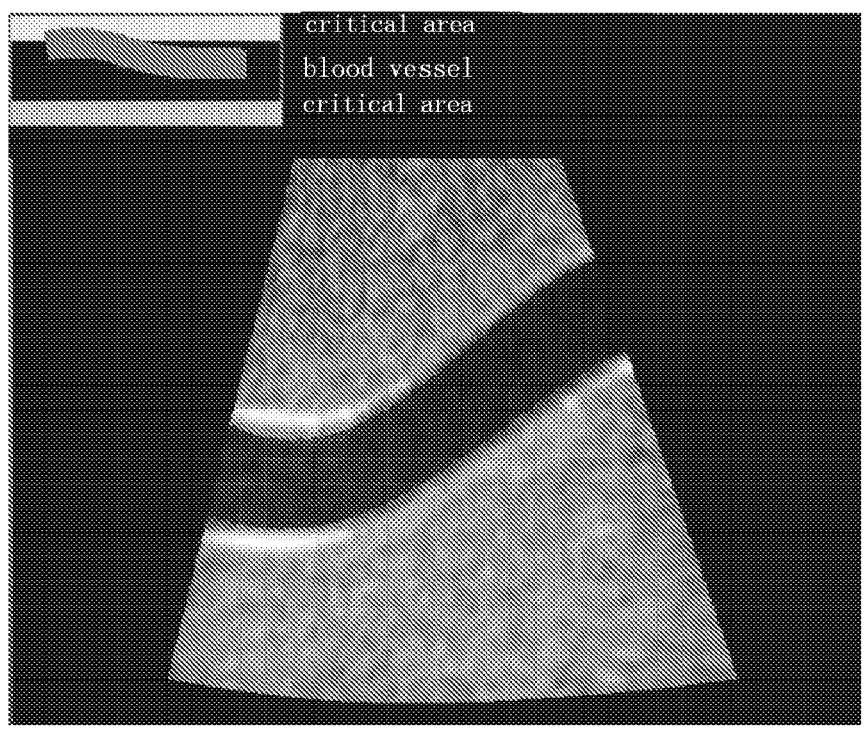

In addition, the ultrasound volume probe navigation and control method further includes displaying the navigation view on a display in real time. As shown in FIGS. 5A and 5B, the navigation view can be displayed on the upper left corner of the ultrasound image, and of course it can be displayed in other places.

As shown in FIG. 3, the size of the scan data matrix can be expressed as:

$$N_{samples} \times N_{beams} \times N_{frames}$$

wherein, in three-dimensional beam space, $N_{samples}$ indicates the number of samples on each beam, $N_{beams}$ indicates the number of beams, $N_{frames}$ indicates the number of frames being scanned when the ultrasound volume probe sweeps (i.e., corresponding to the scan angle).

In one embodiment, the ultrasound volume probe navigation and control method may further include creating a mathematical model of the blood vessel in the scan direction based on the three-dimensional matrix.

As shown in FIG. 3, in three-dimensional beam space, the plane formed by $N_{samples}$ and $N_{frames}$ is a detection plane, so a rectangle can be obtained by intercepting along the detection plane. The two sides of the rectangle are $N_{samples}$ and $N_{frames}$ respectively. An ellipse obtained from within this rectangle is the cross-section of the blood vessel. The ellipse is just the mathematical mode of the blood vessel, which can be expressed by $(x_c, y_c, a, b, \theta)$.

Wherein, a indicates the major axis of the ellipse, b indicates the minor axis of the ellipse, $\theta$ indicates the angle between the major axis of the ellipse and the coordinate axis X, while $(x_c, y_c)$ indicates the center point of the ellipse.

Therefore, the ellipse equation is defined as follows:

$$\frac{(x\cos\theta + y\sin\theta)^2}{a^2} + \frac{(y\cos\theta - x\sin\theta)^2}{b^2} = 1$$

With the above mathematical mode, the projection on the coordinate axis X of a point on the boundary curve of the blood vessel can be calculated based on this mathematical mode as follows:

$$P_X = |a \cos\theta \cos\alpha - b \sin\theta \sin\alpha|$$

wherein, $$\tan\alpha = \frac{b}{a}\tan\theta.$$

Wherein, a indicates the angle between the x axis and the connection line from the point on the ellipse that projects the maximum value at the coordinate axis X and the center of the ellipse.

As shown in FIG. 3, the endpoint coordinates of the projection line segment PX of the ellipse are $(x_c-P_X, i_{beams})$, $(x_c+P_X, i_{beams})$, (i indicates the serial number of the detection plane). All the endpoints of the projection line segment PX of the ellipse in the detection plane together form a projection boundary curve of the whole blood vessel (hereinafter referred to as the boundary curve of the blood vessel). Finally a polynomial fit algorithm can be applied to get a smooth boundary curve of the blood vessel.

If the boundary curve of the blood vessel has an intersection with the critical area, a warning is sent to warn the user that the blood vessel has entered the critical area.

The warning may include changing the color of the critical area and/or making the speaker produce sound. The warning may also include any warnings that are known or that will be known to a person having ordinary skill in the art, as long as an effect of caution can be achieved.

If the blood vessel has entered the critical area, some corresponding measures need to be adopted to alter the scan range to make the blood vessel covered by the scan volume range.

Additionally, during vessel tracking mode, the projection centerline of the blood vessel within every volume data can be obtained through the above mathematical model of the blood vessel. Thus, the shift distance between current centerline of the blood vessel and the previous one can be calculated. This shift distance may be used to further adjust the scan parameters of the volume probe (e.g., volume scan angle and so on).

Figure 6:
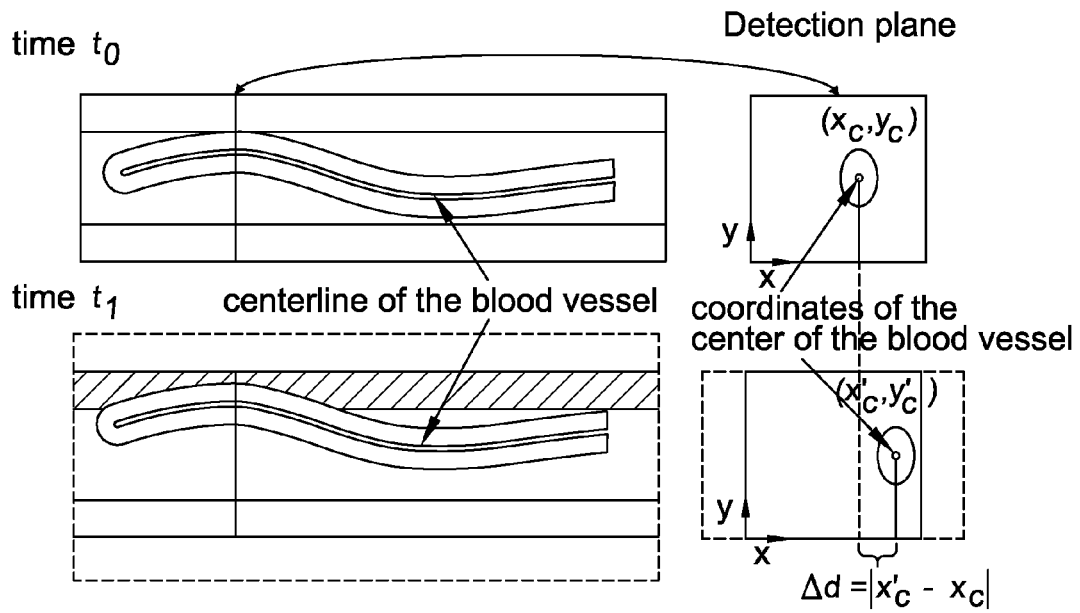
FIG. 6 is a schematic diagram illustrating calculating a shift distance of a centerline of the blood vessel.

As shown in FIG. 6, using the above mathematical model of the blood vessel, the coordinates of the center of the ellipse within each detection plane can be obtained, and all these coordinates within detection planes together form the projection centerline of the blood vessel. Therefore, the shift distance between the centerline of the blood vessel at current time t1 and the centerline of the blood vessel at the previous time t0 (i.e., the maximum value of shift distances of the center coordinates of the ellipses within all detection planes) can be calculated. This shift distance corresponds to the scan angle to be enlarged.

Figure 7:
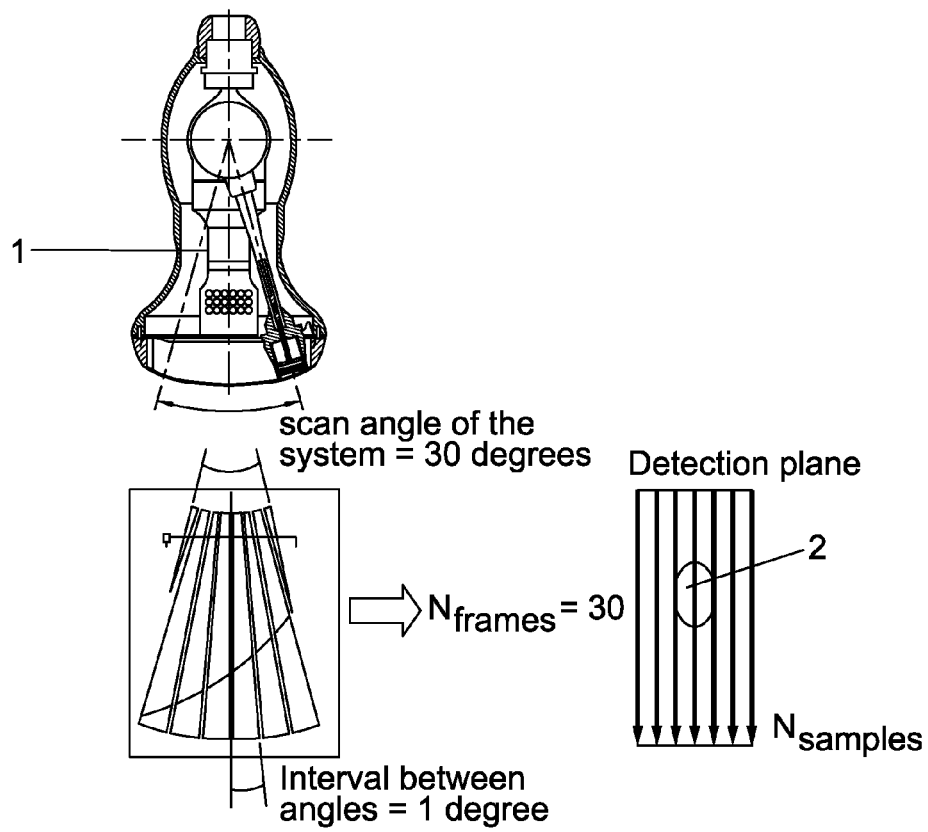
FIG. 7 is a schematic diagram illustrating the relationship between the scan angle of the volume probe and the number of scanned frames.

For example, supposed that the scan angle of a system is equal to 30 degrees, the interval between scan angles is 1 degree. In three-dimensional mode, scan data is obtained, for example, as an 8-bit grayscale image (see the lower left part of FIG. 7). The ultrasound data obtained by scanning is stored in a three-dimensional matrix whose size is Nsamples× Nbeams×Nframes=300×128×30, wherein Nsamples=300, Nbeams=128, and Nframes=30. Nframes indicates the number of frames being scanned when the ultrasound volume probe sweeps (See FIG. 7, the current scan angle of the system is 30 degrees, the interval between scan angles is 1 degree, so the number of scanned frames=30/1=30 frames).

As shown in FIG. 4, a navigation view is obtained by making a downward projection of the three-dimensional matrix. The size of the navigation view is Nbeams× Nframes=128×30, wherein the width of the navigation view is 128, the height thereof is 30.15% of its height is taken to create a critical area, and the size of the critical area can be obtained. The width of each critical area is 128, the height thereof is as follows: 30×0.15=4.5.

At the time t0, the blood vessel is in a normal position, having not entered the critical area.

A three-dimensional image segmentation of the ultrasound data at the time t0 in beam space is performed, and an elliptic model of the blood vessel is created, and a collection of ellipses can be obtained as follows:
{$(x_C, y_C, a, b, \theta)$}={(10, 10, 8, 4, 30.3), (12, 11, 10, 5, 29.5), ... }

The coordinates of projection centerlines of the blood vessel are as follows: {$(x_C, y_C)$}={(10, 10), (12, 11), ... }

At the time t1, the blood vessel enters the critical area. A buzzer (not shown) is used in this example to warn the user.

A three-dimensional image segmentation of the ultrasound data at the time t1 in beam space is performed, and a elliptic model of the blood vessel is created, and a collection of ellipses can be obtained as follows:
{$(x_C, y_C, a, b, \theta)$}={(12, 9, 8, 4, 30.1), (15, 12, 10, 5, 29.8), ... }

The coordinates of projection centerlines of the blood vessel are as follows: {$(x_C, y_C)$}={(12, 9), (15, 12), ... }.

Then shift distance of the centerline of the blood vessel, max{$\Delta d=|x'_c-x_c|$}=max{|12−10|, |15−12|, ... }=3.

Then, at the time t1, the scan angle of the system=30+2× 3=36 degrees.

The ultrasound volume probe is controlled to scan by the calculated new scan angle.

In another aspect, an ultrasound volume probe navigation and control device is provided. The ultrasound volume probe navigation and control device includes a unit for acquiring scan data in a three-dimensional scan mode, a unit for forming a navigation view based on a three-dimensional matrix formed by the scan data in beam space, a unit for determining a critical area on the navigation view and a unit for navigating and controlling the ultrasound volume probe according to whether the blood vessel is in the critical area.

In one embodiment, the ultrasound volume probe navigation and control device further includes a unit for displaying the navigation view on a display in real time.

The scan data can be expressed as:

$$N_{samples} \times N_{beams} \times N_{frames}$$

Wherein, $N_{samples}$ indicates the number of samples on each beam, $N_{beams}$ indicates the number of beams, $N_{frames}$ indicates the number of frames being scanned when the ultrasound volume probe sweeps.

Further, the ultrasound volume probe navigation and control device includes a unit for creating a mathematical model of the blood vessel in the scan direction based on the three-dimensional matrix.

The mathematical model can be expressed as:

$$\frac{(x\cos\theta + y\sin\theta)^2}{a^2} + \frac{(y\cos\theta - x\sin\theta)^2}{b^2} = 1$$

wherein, a indicates the major axis of the ellipse, b indicates the minor axis of the ellipse, and θ indicates the angle between the major axis of the ellipse and the coordinate axis X.

In one embodiment, the ultrasound volume probe navigation and control device further includes a unit for calculating, according to the following formula, the projection on the coordinate axis X of a point on the boundary curve of the blood vessel:

$$P_X = |a \cos\theta \cos\alpha - b \sin\theta \sin\alpha|$$

wherein, $$\tan\alpha = \frac{b}{a}\tan\theta.$$

In one embodiment, the ultrasound volume probe navigation and control device further includes a unit for sending a warning when the boundary curve of the blood vessel has an intersection with the critical area.

The warning includes changing the color of the critical area or making the speaker produce sound.

In one embodiment, the ultrasound volume probe navigation and control device further includes a unit for changing the scan range, if the blood vessel enters the critical area, so that the blood vessel can be included in the scan volume range.

The ultrasound volume probe navigation and control device described herein performs the ultrasound volume probe navigation and control method described herein. Accordingly, the ultrasound volume probe navigation and control device are not discussed in detail herein.

In still another aspect, an ultrasound apparatus is provided, which includes the above mentioned ultrasound volume probe navigation and control device.

The embodiments described herein adopt a three-dimensional scan mode and form a navigation view based on a three-dimensional matrix formed by the obtained scan data in beam space, thereby the vessel positions can be obtained in real time to navigate and control the volume probe, without the scenario of the blood vessel beyond the scan range.

In addition, the embodiments described herein are able to control and adjust the scan parameters according to the vessel positions, and provide a balance between system performance and error tolerance.

Although specific embodiments have been described in combination with the drawings above, a person having ordinary skill in the art can make various changes, modifications and equivalent substitutions without departing from the spirit and scope of the present invention. Such changes, modifications and equivalent substitutions shall fall within the spirit and scope defined by the attached claims.

What is claimed is:

1. An ultrasound volume probe navigation and control method, comprising:
    acquiring scan data in a three-dimensional scan mode;
    forming a navigation view based on a three-dimensional matrix formed by the scan data in beam space;
    determining a critical area on the navigation view; and
    navigating and controlling an ultrasound volume probe based on whether a blood vessel is in the critical area, wherein the critical area is a marginal area of a scan range of the ultrasound volume probe.

2. The ultrasound volume probe navigation and control method according to claim 1, further comprising displaying the navigation view on a display in real time.

3. The ultrasound volume probe navigation and control method according to claim 2, wherein the scan data can be expressed as:

$$N_{samples} \times N_{beams} \times N_{frames}$$

wherein, $N_{samples}$ indicates a number of samples on each beam, $N_{beams}$ indicates a number of beams, and $N_{frames}$ indicates a number of frames being scanned in a sweep of the ultrasound volume probe.

4. The ultrasound volume probe navigation and control method according to claim 3, further comprising creating a mathematical model of the blood vessel in a scan direction based on the three-dimensional matrix.

5. The ultrasound volume probe navigation and control method according to claim 4, wherein the mathematical model is expressed as:

$$\frac{(x\cos\theta + y\sin\theta)^2}{a^2} + \frac{(y\cos\theta - x\sin\theta)^2}{b^2} = 1$$

wherein, a indicates a major axis of an ellipse, b indicates a minor axis of an ellipse, and θ indicates an angle between the major axis of the ellipse and an X coordinate axis.

6. The ultrasound volume probe navigation and control method according to claim 5, further comprising calculating a projection on the X coordinate axis of a point on a boundary curve of the blood vessel, wherein the projection is expressed as:

$$P_X = |a \cos\theta \cos\alpha - b \sin\theta \sin\alpha|$$

wherein, $$\tan\alpha = \frac{b}{a}\tan\theta.$$

7. The ultrasound volume probe navigation and control method according to claim 6, wherein, when the boundary curve of the blood vessel has an intersection with the critical area, a warning is sent.

8. The ultrasound volume probe navigation and control method according to claim 7, wherein the warning includes changing a color of the critical area.

9. The ultrasound volume probe navigation and control method according to claim 7, wherein the warning includes making a speaker produce sound.

10. The ultrasound volume probe navigation and control method according to claim 8, wherein, if the blood vessel enters the critical area, the scan range is changed so that the blood vessel can be included in the scan range.

11. An ultrasound volume probe navigation and control device, comprising:
   a unit configured to acquire scan data in a three-dimensional scan mode;
   a unit configured to form a navigation view based on a three-dimensional matrix formed by the scan data in beam space;
   a unit configured to determine a critical area on the navigation view; and
   a unit configured to navigate and control an ultrasound volume probe based on whether a blood vessel is in the critical area, wherein the critical area is a marginal area of a scan range of the ultrasound volume probe.

12. The ultrasound volume probe navigation and control device according to claim 11, further comprising a unit configured to display the navigation view on a display in real time.

13. The ultrasound volume probe navigation and control device according to claim 12, wherein the scan data can be expressed as:

$$N_{samples} \times N_{beams} \times N_{frames}$$

wherein, $N_{samples}$ indicates a number of samples on each beam, $N_{beams}$ indicates a number of beams, and $N_{frames}$ indicates a number of frames being scanned in a sweep of the ultrasound volume probe.

14. The ultrasound volume probe navigation and control device according to claim 13, further comprising a unit configured to create a mathematical model of the blood vessel in a scan direction based on the three-dimensional matrix.

15. The ultrasound volume probe navigation and control device according to claim 14, wherein the mathematical model is expressed as:

$$\frac{(x\cos\theta + y\sin\theta)^2}{a^2} + \frac{(y\cos\theta - x\sin\theta)^2}{b^2} = 1$$

wherein, a indicates a major axis of an ellipse, b indicates a minor axis of the ellipse, and θ indicates an angle between the major axis of the ellipse and an X coordinate axis.

16. The ultrasound volume probe navigation and control device according to claim 15, further comprising a unit configured to calculate a projection on the X coordinate axis of a point on a boundary curve of the blood vessel, wherein the projection is expressed as:

$$P_X = |a \cos\theta \cos\alpha - b \sin\theta \sin\alpha|$$

wherein, $$\tan\alpha = \frac{b}{a}\tan\theta.$$

17. The ultrasound volume probe navigation and control device according to claim 16, further comprising a unit configured to send a warning when the boundary curve of the blood vessel has an intersection with the critical area.

18. The ultrasound volume probe navigation and control device according to claim 17, wherein the warning includes at least one of changing a color of the critical area and making a speaker produce sound.

19. The ultrasound volume probe navigation and control device according to claim 18, further comprising a unit configured to change the scan range if the blood vessel enters the critical area, such that the blood vessel is included in the scan range.

20. An ultrasound apparatus comprising:
   an ultrasound volume probe; and
   an ultrasound volume probe navigation and control device, wherein the ultrasound volume probe navigation and control device comprises:
   a unit configured to acquire scan data in a three-dimensional scan mode;
   a unit configured to form a navigation view based on a three-dimensional matrix formed by the scan data in beam space;
   a unit configured to determine a critical area on the navigation view; and
   a unit configured to navigate and control the ultrasound volume probe based on whether a blood vessel is in the critical area, wherein the critical area is a marginal area of a scan range of the ultrasound volume probe.

* * * * *